United States Patent [19]

Wei et al.

[11] Patent Number: 4,663,469

[45] Date of Patent: May 5, 1987

[54] 4-HYDROXY-L-THREONINAMIDES

[75] Inventors: Chung-Chen Wei, Cedar Knolls; Manfred Weigele, North Caldwell, both of N.J.

[73] Assignee: Hoffman-La Roche Inc., Nutley, N.J.

[21] Appl. No.: 680,170

[22] Filed: Dec. 10, 1984

Related U.S. Application Data

[62] Division of Ser. No. 448,116, Dec. 9, 1982, Pat. No. 4,502,994.

[51] Int. Cl.$^4$ ............................................. C07D 317/26
[52] U.S. Cl. ..................................... 549/449; 549/229; 549/342; 549/452; 560/145; 560/159
[58] Field of Search ................ 560/145, 159; 549/652, 549/449, 342, 229; 564/198

[56] References Cited

U.S. PATENT DOCUMENTS 4,216,008 8/1980 Weigele et al. ..................... 71/106

FOREIGN PATENT DOCUMENTS 0073061 3/1983 European Pat. Off. .
0076758 4/1983 European Pat. Off. .

OTHER PUBLICATIONS

Floyd et al., "Monobactams, Stereospecific Synthesis . . . ", J. Org. Chem., 47:176–178 (1982).

Barton, "Protective Groups in Organic Chemistry", J. F. W. McOmie, Ed., Plenum Press, New York, N.Y., 1973, pp. 43–93.

Primary Examiner—Nicky Chan
Attorney, Agent, or Firm—Jon S. Saxe; Bernard S. Leon; Mark E. Waddell

[57] ABSTRACT

A novel enantiomeric systhesis from ascorbic acid of (3S,4S)-3-amino-4-carbamoyloxymethyl-2-azetidinone-1-sulfate, an intermediate for an antibiotic compound.

6 Claims, No Drawings

4-HYDROXY-L-THREONINAMIDES

This is a division of application Ser. No. 488,116, filed Dec. 9, 1982, now U.S. Pat. No. 4,502,994.

BACKGROUND OF INVENTION

In U.S. patent application No. 405,592, filed Aug. 5, 1982, there is disclosed the new sulfazecin related antibiotic compound of the formula:

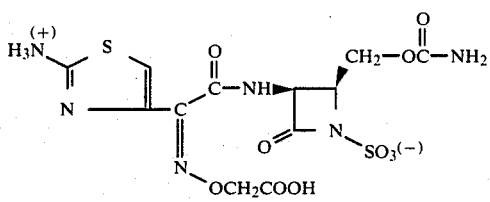

This new antibiotic is similar in activity to the antibiotic azthreonam and useful in treating infectious diseases caused by gram negative microorganisms particularly *P. aeruginosa.*

The compound of formula I is prepared from an intermediate of the formula:

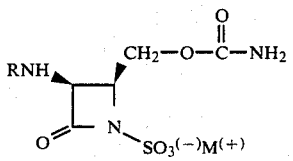

where R is an amino protecting group; and $M^{(+)}$ is a cation.

The compound of formula II is converted to the compound of formula I by first cleaving the protecting group to form a compound of the formula:

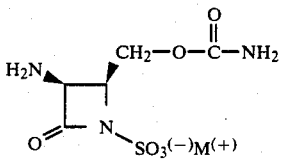

wherein $M^{(+)}$ is as above.
and then reacting the compound of formula III with a compound of the formula:

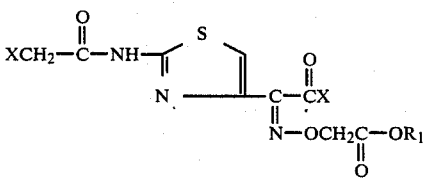

wherein X is halogen and $R_1$ taken together with the oxygen atom to which it is attached forms an ester group convertible to an acid upon hydrolysis or hydrogenolysis
to form a compound of the formula:

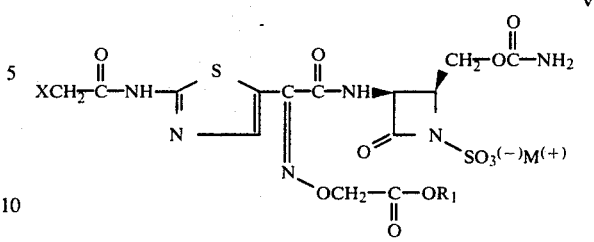

wherein X, $M^{(+)}$ and $R_1$ are as above.

The compound of formula V is treated with a conventional deacylation agent and thereafter the ester group $R_1$ is removed by either hydrolysis or hydrogenolysis to produce the compound of formula I.

A problem which has occurred with the above synthesis is that it has been difficult to synthesize the compound of formula II in its enantiomeric form efficiently and effectively from a readily available and economic starting material.

SUMMARY OF INVENTION

In accordance with this invention, there is provided a simple and economic synthesis of the compound of formula II in its enantiomeric form from ascorbic acid. Ascorbic acid (Vitamin C) is a economical starting material which is readily available.

DETAILED DESCTIPTION

The term "lower alkyl" designates monovalent saturated straight or branched aliphatic hydrocarbon groups containing from 1 to 7 carbon atoms such as ethyl, methyl, n-propyl, isopropyl, n-butyl, isobutyl, tert-butyl, with methyl and ethyl being preferred. The term "lower alkylene" designates a divalent saturated aliphatic straight chain hydrocarbon radical containing from 2 to 7 carbons such as ethylene, butylene, pentylene, etc. The term "halogen" includes all four halogens such as chlorine, bromine, fluorine and iodine with chlorine and bromine being preferred. The term "lower alkanoyl" designates alkanoyl groups derived from aliphatic monocarboxylic acids containing from 2 to 7 carbon atoms such as acetyl, propionyl, butyryl, pivaloyl, etc.

The term "lower alkoxy" denotes lower alkoxy groups containing from 1 to 7 carbon atoms such as methoxy, ethoxy, n-butoxy, isopropoxy, etc. The term "halo lower alkyl" denotes lower alkyl groups defined hereinbefore where the lower alkyl group is substituted in one or more positions with a halogen substituent such as trifluoromethyl, 2-chloroethyl, chloromethyl, 2-chloro-1-fluoroethyl, etc. The term halo substituted lower alkoxy designates lower alkoxy substituents as defined hereinabove which are substituted on one or more positions with a halogen substituent such as chloromethoxy, 2,2-dichloroethoxy, etc.

As also used herein, the term "aryl" signifies mononuclear aromatic hydrocarbon groups such as phenyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, etc., which can be unsubstituted or substituted with one or more of the aforementioned groups. The preferred aryl groups are the substituted and unsubstituted mononuclear aryl groups, particularly phenyl. The term "aralkyl" designates aryl lower alkyl groups wherein aryl and lower alkyl are as defined above, particularly benzyl. The term "aroyl" comprehends aryl carbonyl groups wherein aryl is defined as above particularly benzoyl and substituted benzoyl, i.e. nitrobenzoyl, chlorobenzoyl, etc.

When aryl is a substituted phenyl group the preferred substituted phenyl radicals are those such as a mono substituted phenyl group or disubstituted phenyl group where the disubstitution occurs in the 2,4 or 2,6 positions or, most preferably, in the 3,4 position of the phenyl moiety. Suitable mono-substituents include halogen, lower alkyl, nitro, or lower alkoxy substituents which are preferably substituted in the 2-position of the phenyl moiety. Suitable di-substituents are 2,4 or 2,6 dihalophenyl; 2-halo, 4 or 6 nitro phenyl as well as 2,4-dimethoxy phenyl.

The term "aryloxy" designates aryloxy groups wherein aryl is defined as above, particularly phenoxy, halo substituted phenoxy, nitro substituted phenoxy and lower alkyl substituted phenoxy. The term "lower alkoxycarbonyl" designates lower alkoxycarbonyl groups wherein lower alkoxy is defined as above such as methoxycarbonyl, ethoxycarbonyl, etc. The term aryl-loweralkyloxycarbonyl designates arylloweralkoxycarbonyl groups when aryl and lower alkoxy are defined as above, particularly phenylloweralkoxycarbonyl, and substituted phenyl lower alkoxy carbonyl, and especially benzyloxycarbonyl, nitrobenzyloxycarbonyl, lower alkyl substituted benzyloxycarbonyl, halobenzyloxycaerbonyl. The term "lower alkoxycarbonyl" designates lower alkoxycarbonyl substituents wherein lower alkoxy is defined as above, particularly methoxycarbonyl. The term "halo substituted lower alkoxy carbonyl" designates halo substituted lower alkoxy carbonyl substituents wherein halo and lower alkoxy are defined as above.

When an amino protecting group is used in the synthesis of this invention, any conventional amino protecting group can be utilized. Any of the conventional amino protecting groups which can be removed by conventional acid hydrolysis or catalytic hydrogenation are preferred for use in the compounds of this invention. These conventional amino protecting groups include lower alkoxy carbonyl, aryloxycarbonyl, halo substituted lower alkoxy carbonyl and arylloweralkoxycarbonyl. Among the preferred amino protecting groups are included benzyloxycarbonyl, t-butoxycarbonyl, etc.

The term "alkali metal" includes all of the alkali metals such as lithium, sodium, potassium, etc. The term "alkaline earth metal" includes all of the conventional alkaline earth metals such as calcium, magnesium, etc.

In the first step of this synthesis, ascorbic acid is converted to a compound of the formula:

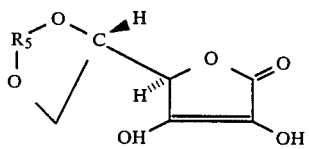

VI wherein $R_5$ taken together with its attached oxygen atoms forms a ketal or acetal protecting group.

In accordance with this invention, $R_5$ taken with its attached oxygen atom can form any conventional acetal or ketal protecting group. In accordance with a preferred embodiment, the divalent radical $R_5$ is

where $R_6$ and $R_7$ can be hydrogen, lower alkyl, aralkyl, aryl, lower alkoxy, lower alkyl or aryloxy, or taken together form oxo or lower alkylene. Among the preferred substituents for $R_6$ and $R_7$ are lower alkyl, lower alkoxy, phenyloxy, halosubstituted phenyloxy, nitrosubstituted phenylowy, phenyl, halophenyl, nitrophenyl, phenylloweralkyl, halophenylloweralkyl and nitrophenylloweralkyl as well as $R_6$ and $R_7$ taken together with the attached carbon alone forming lower alkylene or forming oxo.

The compound of formula VI can be formed from ascorbic acid by conventional means such as by reacting ascorbic acid with a suitable aldehyde or ketone or acetal or ketals thereof. In forming the compound of formula VI, from ascorbic acid, in accordance with this invention, any aldehyde or ketone can be utilized. Among the preferred aldehydes or ketones which can be utilized in accordance with this invention, are included, methyl-ethyl-ketone, formaldehyde, acetaldehyde, benzylaldehyde, dibenzyl ketone, diphenylethyl ketone, cycloheptanone, cyclohexanone, etc. The preferred ketone is acetone. To form the compound of formula VI where $R_6$ and $R_7$ taken together form oxo, ascorbic acid is reacted in a conventional manner with phosgene or 1,1'-carbonyldiimidazole.

The compound of formula VI is converted to a compound of formula II via the following intermediates:

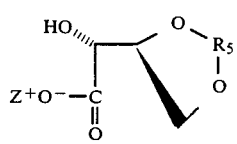

VII

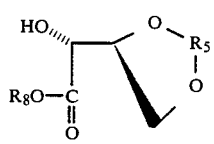

VIII

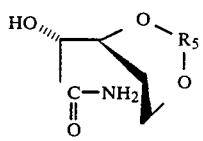

IX

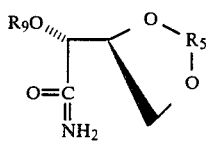

X

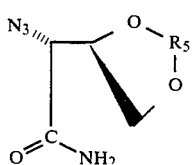

XI

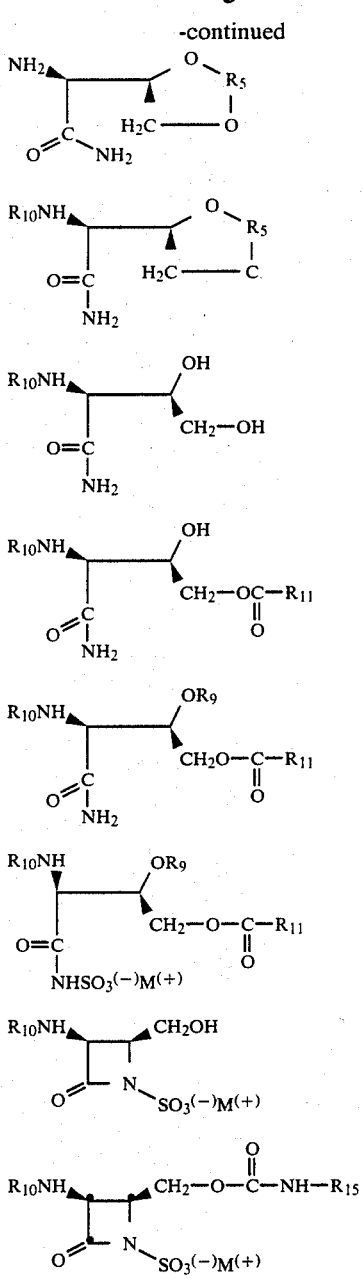

wherein $M^{(+)}$ and RLHd 5 are as above; $R_8$ is lower alkyl; $R_9$ taken together with its attached oxygen atom forms is a leaving group; $R_{10}$ is an amino protecting group; $R_{11}$ is hydrogen, lower alkyl, haloloweralkyl or aryl, and $Z^{(+)}$ is a cation of an alkali metal or alkaline earth metal; $R_{15}$ is lower alkanoyl, halo-substituted lower alkanoyl, aryl carbonyl, dichlorophosphoryl or dimethoxyphosphoryl.

The compound of formula VI is converted to the compound of formula VII by treating the compound of formula VI with an oxidizing agent in the presence of a base. In carrying out this reaction, it is generally preferred that hydrogen peroxide be utilized as the oxidizing agent and an alkaline earth metal base be utilized such as calcium carbonate. In carrying out the reaction with hydrogen peroxide, it is generally preferred to utilize an aqueous medium at temperatures below 40° C., preferably from about 20° C. to 30° C. The compound of formula VII is formed as a salt depending upon the particular base used. In the case where an allkaline earth metal base such as calcium is used, the calcium salt of the compound of formula VII is produced.

The compound of formula VII is converted to the compound of formula VIII by esterifying the compound of formula VII to form the lower alkyl ester thereof. Any conventional method of esterifying the compound of formula VII with a lower alkyl group can be utilized to carry out this conversion. Generally, this conversion can be carried out by reacting the compound of formula VII with a lower alkyl halide, preferably a lower alkyliodide, in an aqueous medium containing an organic solvent such as dimethylformamide or a lower alkanol. Preferably, lower alkanols containing the alkyl group used to form the ester of the compound of formula VII is utilized in the solvent. In carrying out this reaction, temperature and pressure are not critical and this reaction can be carried out at room temperature and atmospheric pressure. If desired, higher or lower temperatures can be utilized. Esterification can be also carried out by utilizing a lower dialkyl sulfate such as dimethylsulfate.

The compound of formula VIII is converted to the compound of formula IX by forming the amide of formula VIII. Any conventional method of converting an ester to an amide can be utilized in carrying out this reaction. Among the preferred methods of forming amides is by treating the compound of formula VIII with ammonium hydroxide in an aqueous medium which may contain organic solvents such as tetrahydrofuran dioxane or lower alkanols at temperatures of from $-10°$ to 0° C.

The compound of formula IX is converted to the compound of formula X by converting the free hydroxy group in the compound of formula IX to a leaving group. Any conventional leaving group can be utilized. Among the preferred leaving groups are those where $R_9$ is lower alkyl sulfonyl groups such as mesyl, aryl sulfonyl groups such as tosyl, halophenylsulfonyl, i.e. ortho or para-chlorosulfonyl, and the trihalo lower alkyl sulfonyl groups such as trifluoromethyl sulfonyl. Any of conventional procedures known to convert the hydroxy group to these leaving groups can be utilized.

The compound of formula X is converted to the compound of formula XI by treating the compound of formula X with an alkali metal azide in an inert organic solvent. In carrying out this reaction, any conventional inert organic solvent, such as the aprotic solvents can be utilized. Among the preferred aprotic solvents for carrying out this reaction are dimethylformamide and lower alkanols. In carrying out this reaction, temperature and pressure are not critical and the reaction may be carried out at room temperature and atmospheric pressure. On the other hand, higher or lower temperatures can, if desired, be utilized.

The compound of formula XI is converted to the compound of formula XII by hydrogenation. Any conventional method of hydrogenation can be utilized to convert the compound of formula XI into the amine of formula XII. Among the preferred hydrogenation catalysts for carrying out this reaction is palladium on carbon. Any of the conditions conventional in carrying out this type of hydrogenation can be utilized in this conversion.

The compound of formula XII is converted to the compound of formula XIII by protecting the amino substituent with a suitable amino protecting group. Any of the conventional amino protecting groups can be utilized to carry out this conversion. Among the preferred amino protecting groups are included lower alkoxycarbonyl, aryloxycarbonyl, halo substituted lower alkoxycarbonyl, and aryl lower alkoxycarbonyl with benzyloxycarbonyl being especially preferred. Any conventional method of protecting an amino substituent can be utilized in carrying out this conversion. Among the preferred methods is reacting the specific carbonyl halide, with the compound of formula XII. The compound of formula XIII is converted to the compound of formula XIV by hydrolysis utilizing very mild conditions such as dilute aqueous inorganic acid at room temperature, and organic solvent such as acetonitrile. Among the dilute inorganic acids which can be utilized are included dilute aqueous hydrochloric acid. Care should be taken in carrying out this reaction so that the protecting group on the amino substituent does not hydrolyze. This hydrolysis will remove the ketal or acetal protecting group designated by $R_5$. In carrying out this reaction, care should also be taken so that high temperatures, i.e. above 30° C. are not utilized. In this manner removal of the amino protecting group $R_{10}$ will be avoided. Generally, it is preferred to carry out this reaction at room temperature.

The compound of formula XIV is reacted to form the compound of formula XV by reaction with an acid halide of the formula

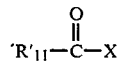

wherein $R'_{11}$ is lower alkyl, halo substituted lower alkyl or aryl, and X is halogen
to esterify the primary alcohol moiety. Any of the conditions conventional in esterifying primary alcohol with an organic acid can be utilized to carry out this reaction. Among the preferred acid halides are the halides of lower alkanoic acids, halosubstituted lower alkanoic acids, and the aroic acids, i.e. benzoic acid, nitrobenzoic acid, halobenzoic acid, etc. On the other hand, the compound of formula XIV can be converted to the compound of formula XV by reacting the compound of formula XIV with an anhydride of the formula

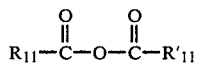

wherein $R_{11}$ and $R'_{11}$ are as above.

The compound of formula XV is converted to the compound of formula XVI by converting the secondary hydroxy substituent to a leaving group as described in connection with the formation of the compound of formula X. The preferred leaving group for this reaction is lower alkyl sulfonyl, preferably mesyl.

The compound of formula XVI is converted to the compound of formula XVII by reacting the compound of formula XVI with a complex of the formula $Y.SO_3$                        XX wherein Y is a N-heteroaromatic base or an amide.
In accordance with this invention, Y can be any of the conventional heteroaromatic bases or amide. Among the preferred heteroaromatic bases are included picoline pyridine and quinoline. Among the preferred amides, dimethylformamide is especially preferred. If Y is a heteroaromatic base, the compound of formula XVII is obtained as a salt of said base, where $M^{(+)}$ is $YH^{(+)}$. If desired this salt can subsequently be converted to any other salt form by conventional means.

On the other hand, where other bases are utilized, $M^{(+)}$ will represent the cation of these other bases. Among the other cations which $M^{(+)}$ can represent are included the alkali metals such as sodium, potassium and lithium, ammonium and protonated amines such as tertiary lower alkyl amines, for example triethylamine; hydroxyloweralkyl amines, for example 2-hydroxyethylamine, bis-(2-hydroxyethyl)amine, tris-(2-hydroxyethyl)amine; cycloamines, for example dicyclohexyl amines; or benzylamines, for example N,N'-dibenzylethyleneamine, and dibenzylamine. Furthermore, $M^{(+)}$ can be any conventional quaternary ammonium ion such as the tetralower alkyl ammonium ion such as tetrabutyl ammonium, tetramethyl ammonium, dimethyl diethyl ammonium, etc.

The compound of formula XVII in any suitable basic form is converted to the compound of formula XVIII by treatment with alkali metal carbonate or alkali metal bicarbonate in a two-phase solvent system. In carrying out this reaction, any conventional alkali metal carbonate and bicarbonate can be utilized. The aqueous solution of the alkali metal bicarbonate or carbonate provides the aqueous phase for this reaction. The solvent system also contains a organic phase formed from a conventional inert organic solvent. Any conventional aprotic solvent such as a halogenated hydrocarbon solvent can be utilized in carrying out this reaction. Treatment of the compound of formula XVII with an aqueous alkali metal base removes the leaving group and deacylates the organic acid functional group to form the cyclized product of formula XVIII. In converting the compound of formula XVIII to the compound of formula XXI, it is preferred that M be a quaternary ammonium ion, particularly a tetrabutyl ammonium ion.

In converting the compound of formula XVIII to the compound of formula XXI, the compound of formula XVIII, preferably in its quaternary ammonium salt form, is reacted with an isocyanide of the formula:

$R_{15}-N=C=O$                    XXII wherein $R_{15}$ is lower alkanoyl, halo substituted lower alkanoyl, arylcarbonyl, chlorophosphoryl, or dimethoxyphosphoryl.

The compound of formula XVIII is reacted with the compound of formula XXII to produce the compound of formula XXI in an aprotic solvent. Any of the conventional aprotic solvents can be utilized in carrying out this reaction. Among the preferred aprotic solvents are the halogenated hydrocarbons such as ethylene dichloride, methylene chloride and ethers such as diethyl ether and tetrahydrofuran. In carrying out his reaction, temperature and pressure are not critical and this reaction caun be carried out at room temperature and atmospheric pressure. In fact any temperature of from −20° C. to 30° C. can be utilized in carrying out this reaction.

The compound of formula XXI is converted to the compound of formula II by treating the compound of formula XXI with a deacylating agent. Any conventional deacylating agent can be utilized. Among the preferred deacylating agents are alkali metal organic and inorganic salts such as the alkali metal salts of lower alkyl dithiocarbamates. On the other hand alkali metal salts such as alkali metal carbonate and bicarbonates can also be utilized in carrying out this reaction. Generally the deacylation reaction occurs an aqueous media which may contain an inert organic solvent. Any inert organic solvent can be present in the aqueous media. Among the preferred solvents are the polar solvents such as the lower alkanols. In carrying out this reaction, temperature and pressure are not critical. This reaction can be carried out at room temperature and atmospheric pressure. On the other hand, temperatures of from 0° C. to 60° C. can be utilized with temperatures of from about 20° C. o 40° C. being preferred.

In accordance with an embodiment of this invention, the compound of formula IX can be prepared from ascorbic acid via the following intermediates:

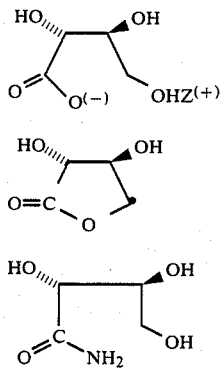

XXVI

XXVII

XXVIII wherein Z is as above.

Ascorbic acid is converted to the compound of formula XXVI utilizing the same conditions described in conversion with the compound of formula VI to the compound of formula VII. The compound of formula XXVI is then converted to the compound of formula XXVII by treating the compound of formula XXVI with a strong acid catalyst in an inert organic solvent. This reaction is carried out at reflux. In carrying out this reaction, any conventional strong acid can be utilized as the cyclization catalyst. Among the preferred strong acids are para-toluene sulfonic acid, hydrochloric acid, etc. In carrying out this reaction, any conventional inert organic solvent can be utilized, with the preferred solvent being acetonitrile. This reaction is carried out at the reflux temperature of the reaction medium.

The compound of formula XXVII is converted to the compound of formula XXVIII by treating the compound of formula XXVII with ammonia. Generally this reaction is carried out in an inert organic solvent such as a lower alkanol and by saturating the solvent medium with ammonia gas. In carrying out this reaction, temperature and pressure are not critical and this reaction can be carried out at room temperature and atmospheric pressure.

The compound of formula XXVIII is converted to the compound of formula IX by reacting the compound of formula XXVIII with a compound of formula:

wherein $R_{16}$ is lower alkyl and $R_5$ is as above.

Generally this reaction is carried out utilizing a strong organic acid as a catalyst. Among the preferred strong organic acids are included paratoluene sulfonic acid is preferred. This reaction is carried out in the presence of an aprotic solvent. Any conventional aprotic solvent can be utilized. Among the preferred aprotic solvents are the solvents mentioned hereinbefore, particularly dimethylformamide, diglyme, halogenated hydrocarbons, N,N-dimethyl acetamide. In carrying out this reaction, temperature and pressure are not critical and this reaction can be carried out at room temperature and atmospheric pressure. In general, temperatures are from 0° C. to 30° C. are preferred in carrying out this reaction.

In accordance with still another embodiment of this invention, the compound of formula XIV can be converted to the compound of formula II via the following intermediates:

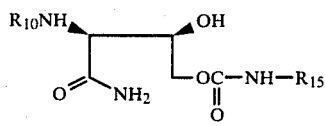

XXX

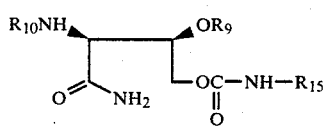

XXXI

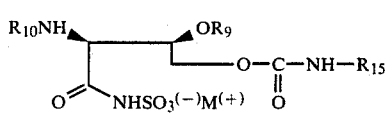

XXXII

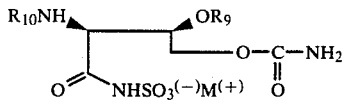

XXXIII wherein $R_9$, $R_{10}$, $R_{15}$, $M^{(+)}$ are as above.

The compound of formula XIV can be converted to the compound of formula XXX by reacting the compound of formula XIV with the isocyanide of formula XXII. This reaction can be carried out in the same manner as described in the conversion of a compound of formula XVIII to the compound of formula XXI. The compound of formula XXX is converted to the compound of formula XXXI by converting the free hydroxy substituent in the compound of formula XXX to a leaving group. Any method for forming the leaving groups as disclosed hereinbefore can be utilized in carrying out this reaction. The compound of formula XXXI is converted to the compound of formula XXXII by reacting the compound of formula XXXI with the compound of formula XX and, if desired, converting the product to the salt. This reaction is carried out in the same manner as described in connection to the conversion of the compound of formula XVI to the compound of formula XVII.

Generally in converting the compound of formula XXXII to the compound of formula XXXIII in the step of this process $M^{(+)}$ is preferably a quaternary ammonium salt, particularly the tetrabutyl ammonium salt or an alkaline metal salt. The compound of formula XXXII is converted to the compound of formula XXXIII by deacylation. Any conventional method of deacylation can be utilized such as disclosed hereinbefore in connection with the conversion of the compound of formula XXI to the compound of formula II.

In the next step of this process, the compound of formula XXXIII is converted to a mixture containing a compound of formula II and the compound of formula XVIII by treating the compound of formula XXXIII with an alkali metal carbonate or bicarbonate in the manner described in connection with cyclization of the compound of formula XVII to the compound of formula XVIII. Generally it is preferred to carry out this reaction in an aqueous alkali metal bicarbonate, particularly sodium bicarbonate. The resultant product of this cyclization is a mixture containing the compound of formula II and XVIII. These compounds may be separated by the conventional means and converted to the compound of formula I in the manner described hereinbefore.

The invention is further illustrated in the following Examples. In the Examples the ether is diethyl ether; THF is tetrahydrofuran; DMF is dimethylformamide; Diaiion is a styrene divinylbenzene polymer; Dowex AGI-X4 is a strongly basic anion exchange resin composed of a quaternary ammonium group attached to a styrene divinylbenzene polymer. AG50W-X4 is a strongly acidic cation exchange resin composed of sulfonic acid attached to a styrene divinylbenzene polymer latex.

EXAMPLE 1

5,6-O-isopropylidene L-ascorbic acid

In a 12-L round bottom flask was placed 8,000 mL acetone, 1,600 g L-ascorbic acid, 1,880 mL 2,2-dimethoxypropane and the mixture was stirred for ¼ hr; hydrogen chloride was added slowly through bubbler over 2–4 min (color of solution changed from colorless to dark yellow). The mixture was stirred for 1 hr and became very viscous. The product was filtered, washed with cold acetone and the solid was then air dried in hood to give 1,521 g of 1st crop of 5,6-O-isopropylidene-L-ascorbic acid. The mother liquor was concentrated to give 225 g of 2nd crop and 162 g of 3rd crop of 5,6-O-isopropylidene-L-ascorbic acid.

EXAMPLE 2

Calcium 3,4-O-isopropylidene-L-threonate

A suspension of 86.4 g (0.4 mole) 5,6-isopropylidene-L-ascorbic acid in 1.0 L water in a 5.0 L 3-necked round bottom flask was treated with 80.0 g (0.8 mole) calcium carbonate (gassing). The resulting mixture was cooled in an ice bath. Then were added dropwise 160 mL (1.6 mole) 30% by volume aqueous hydrogen peroxide. After the addition, the mixture was allowed to slowly warm to about 20° C. (exothermic). The temperature was kept below 30° C. with cooling; when the reaction had subsided, the mixture was heated at 30°–40° C. for 30 min. To the reaction mixture was added 16.0 g charcoal and 1.0 g 10% by weight palladium on 90% by weight carbon to decompose the excess hydrogen peroxide. After this addition, the reaction mixture was heated on a steam bath until a negative test to potassium iodide paper was obtained (30 min). The suspension was filtered through diatomaceous earth. The filtrate was concentrated by rotary evaporation. The residue was recrystalized from water-acetone to afford calcium 3,4-O-isopropylidene-L-threonate 48.4 g white crystals (mp 250° C.).

EXAMPLE 3

Methyl 3,4-O-isopropylidene-L-threonate

A suspension of 23.4 g (0.12 mole) calcium 3,4-O-isopropylidene-L-threonate in 150 mL dimethyl acetamide in a 5000 mL round bottom flask under argon, protected from light, was treated with 73.2 g (0.87 mole) sodium bicarbonate and 67.2 mL (1.08 mole) methyl iodide. The mixture was stirred at room temperature for 2 days. It was then poured into 1200 mL ethyl acetate, the resulting precipitate was filtered. The filtrate was concentrated on a rotovapor to remove ethyl acetate and then the dimethyl acetamide was removed under high vacuum. The residue was taken up in 500 mL ethyl acetate and the resulting solution washed with 2×250 mL brine. Each brine wash was back-extracted with the same 200 mL ethyl acetate. The organic extracts were combined, dried ($Na_2CO_4$), and evaporated on a rotovapor and then under high vacuum to give 21.7 g of a methyl 3,4-O-isopropylidene-L-threonate as light yellow oil. The material was used without further purification in the next step.

EXAMPLE 4

3,4-O-isopropylidene-L-threonamide

Into a 1.0 L round bottom flask was placed 21.6 g of methyl 3,4-O-isopropylidene-L-threonate, 280 mL tetrahydrofuran, and 95 mL 29% by weight aqueous ammonium hydroxide. The reaction mixture was cooled in an ice bath and ammonia gas was bubbled in for 5 min. The solution was then stirred at room temperature overnight. The reaction mixture was concentrated in vacuo and azeotroped with absolute ethanol. The residue was recrystallized from ethyl acetate-hexane to give 17.7 g of 3,4-O-isopropylidene-L-threonamide white crystals (89%), mp 77°–79° C.

EXAMPLE 5

2-Azido-2-deoxy-3,4-O-isopropylidene-L-erythronamide

To a mixture of 3,4-O-isopropylidene-L-threonamide 1.6 g (9.1 mM) in 15 mL 1,2-dichloroethane (dry) and 2 mL pyridine (dry) was added 1.7 mL (10 mM) trifluoromethanesulfonic anhydride slowly at −10° C. (acetone ice). The reaction mixture was stirred at −10° C. for 30 min and then at 0° C. for an additional 30 min. To the reaction 50 mL ether was added, the mixture was washed with brine, dried ($Na_2SO_4$), and evaporated to give 2-O-trifluoromethanesulfonyl-3,4-O-isopropylidene-L-erythronamide. To the crude product in 15 mL dimethyl formamide at 0° C. was added 1.2 g (24 mM) lithium azide and stirred at room temperature for 15 hr. To the reaction 100 mL ethyl acetate was added, washed with brine twice, dried ($Na_2SO_4$) and evaporated to dryness. The crude azido product was purified by flash chromaotography [$SiO_2$; EtOAc-hexane (1:1)] to give 1.3 g of the product (72%). Recrystallization from ether-hexane (1:1 parts of volume) gave the purified product, 2-azido-2-deoxy-3,4-O-isopropylidene-L-erythronamide, 1.24 g, mp 98°–99° C.

EXAMPLE 6

2-O-Benzyloxycarbonyl-amino-2-deoxy-3,4-O-isopropylidene-L-erythronamide

A solution of 12.3 g (0.061 mole) 2-azido-2-deoxy-3,4-O-isopropylidene-L-erythronamide in 500.0 mL ethanol was hydrogenated in the presence of 1.3 g 10% by weight palladium on 90% by weight carbon at 25° C. and atmospheric pressure for 2 hour (the system was evacuated and refilled with hydrogen three times). The mixture was filtered through diatomaceous earth and the catalyst was washed with ethanol (75 mL). The combined filtrate and wash was evaporated to dryness under vacuum to give 2-amino-2-deoxy-3,4-O-isopropylidene-L-erythronamide as a white solid. This white solid was dissolved in 250.0 mL methylene chloride and 8.48 g (0.061 mole) potassium carbonate in 200.0 mL water was added. The mixture was mechanically stirred and cooled to 0° C. After cooling, 11.3 mL (0.079 mole) benzyl chloroformate was added slowly and the mixture allowed to stir 2 hours at 0° C. The white precipitate was filtered. The filtrate was concentrated in vacuum to remove the organic portion which then gave a second precipitate. The combined precipitates were recrystallized from hot ethyl acetate (700 mL), affording 2-benzyloxycarbonyl-amino-2-deoxy-3,4-O-isopropylidene-L-erythronamide as white crystals; mp 181°-142° C., 15.7 g.

EXAMPLE 7

Nα-Benzyloxycarbonyl-4-hydroxy-L-allo-threoninamide

A mixture of 6.44 g (0.021 mole) 2-benzyloxycarbonyl-amino-2-deoxy-3,4-O-isopropylidene-L-erythronamide and a stock solution 418.0 ml [6.6 mL 2N HCl and 13.3 mL water diluted to 900 mL with acetonitrile] was stirred vigorously at room temperature for 2 hours; cooled to 0° C. for 20 minutes and filtered to give 4.65 g of the Nα-benzyloxycarbonyl-4-hydroxy-L-allo-threoninamide mp 175°-176° C., (83%); TLC (8/1 parts by volume methylene chloride/methanol). The above filtrate was recharged with the 6.44 g (0.021 mole) starting amide and the reaction repeated to give the above product. To the filtrate was added propylene oxide (2 mL), then the volume was reduced in vacuo to 200 mL. The solution was placed in the refrigerator overnight and the resulting precipitate was filtered to give an additional 1.0 g yield of Nα-benzyloxycarbonyl-4-hydroxy-L-allo-threoninamide.

EXAMPLE 8

(2S,3S)-2-Benzyloxycarbonylamino-3-methanesulfonyloxy-4-chloroacetoxybutanamide

A solution of Nα-benzyloxycarbonyl-4-hydroxy-L-allothreoninamide 4.08 g (15 mM) in dimethylformamide 40 mL and 2 mL 2.6-lutidine was cooled to −10° C. and 18 mL 1M solution of chloroacetyl chloride in methylene chloride were added slowly. The reaction was stirred at −10° C. for 1 hour, 0° C. for ½ hour, and then concentrated under high vacuum at room temperature to about 15 mL dimethylformamde solution of (2S,3S)-2-benzyloxycarbonylamino-3-hydroxy-4-chloroacetoxybutanamide. To this was added, at −15° C. with stirring, 25 mL dichloroethane, 6.2 mL (45 mM) triethylamine and slowly 2.3 mL (30 mM) methanesulfonyl chloride. The reaction mixture, after stirring at −15° C. to −10° C. for 1 hour, was diluted with 200 mL ethyl acetate, washed with dil. aqueous HCl, brine, and dried over anhydr. NaSO₄. Evaporation at reduced pressure and room temperature gave an oil which was purified on high performance liquid chromatograph (ethyl acetate-hexane, 7:3 parts by volume) to give (2S,3S)-2-benzyloxycarbonylamino-3-methanesulfonyloxy-4-chloroacetoxybutanamide. The analytical sample was crystallized from ethyl acetate hexane, mp 140°-142° C.

EXAMPLE 9

Sodium (3S,4S)cis-3-Benzyloxycarboxamido-4-hydroxymethyl-2-azetidinone-1-sulfonate A solution of 3.0 mL (30 mmole) 2-picoline in 40.0 mL dichloromethane under argon was cooled to −10° C. and to it was added slowly 1.0 mL (15 mmole) chlorosulfonic acid. Stirring was continued −10° C. for 5 minutes. To the solution was then added (2S,3S)-2-benzyloxycarbonylamino-3-methanesulfonyloxy-4-chloroacetoxybutanamide, 2.17 g (5.1 mmole). After stirring at room temperature for 5 minutes, the reaction mixture was refluxed overnight (19 hours) to produce picolinium (2S,23S)-2-benzyloxycarbonylamino-3-methanesulfonyloxy-4-chloroacetoxybutanamide N-sulfonate. After cooling, the reaction mixture was washed with 40 mL 0.6M aqueous potassium bisulfate and extracted with 2×25 mL 2% by weight of an aqueous solution of sodium bicarbonate. The combined bicarbonate extracts were treated with 2.84 g (7 mmole) tetra-n-butyl ammonium hydrogen sulfate and extracted with 2×25 mL dichloromethane. The combined organic extracts were dried (Na₂SO₄), then evaporated to give tetra-n-butyl-ammonium (2S,3S)-3-benzyloxycarboxamido-3-methanesulfonyloxy-4-chloroacetoxybutanamide N-sulfonate at reduced pressure as an amber foam. To a solution of the above foam in 40.0 mL of 1.2 dichloroethane was added 2.0 g (20 mmole) potassium bicarbonate in 25 mL water. The resulting two phase system was stirred vigorously and heated to reflux for 15 minutes (oil bath 80°-85° C.). Upon cooling, the organic layer was separated and the aqueous layer was extracted with dichloromethane. The combined organic extracts were dried (Na₂SO₄) then evaporated at reduced pressure to give tetra-n-butylammonium 3-benzyloxycarboxamido-4-hydroxymethyl-2-azetidinone-1-sulfonate as an amber oil, which was used for the next step without further purification. A portion of the tetra-n-butylammonium salt was converted to the sodium salt by stirring with AG 50W-X4 (Na⁺ form). Purification on Diaion gave the pure sodium (3S,4S)-3-benzyloxycarboxamido-4-hydroxymethyl-2-azetidinone-1-sulfonate.

EXAMPLE 10

Sodium (3S,4S)-cis-3-benzyloxycarboxamido-4-carbamoyloxymethyl-2-azetidinone-1-sulfonate A solution of 2.42 g (4.2 mM) tetrabutylammonium (3S,4S)-cis-3-benzyloxycarboxamido-4-hydroxy-methyl-2-azetidinone-1-sulfonate in 40 mL dry methylene chloride, was cooled to 0° C., and 0.42 mL (8.4 mM) chloroacetylisocyanate was added slowly under argon. The reaction was stirred at 0° C. for 1 hr and 1.2 g (8.16 mM) sodium N-methyl dithiocarbamate in 15 mL water was added. The mixture was stirred vigorously at room temperature for 1 hr. The organic layer was separated and the aqueous phase was extracted once with methylene chloride. The combined organic extracts were dried over Na₂SO₄ and stripped to dryness under reduced pressure. The residue was dissolved in 40 mL ethanol-water (1:2 parts by volume) and stirred with 30 mL AG 50 W-X4 resin (100–200 mesh, Na⁺ form) for 15 min. The resin was filtered off and washed with 30 mL water. The filtrate was concentrated, under high vacuum, to about half of the original volume and washed twice with 10 mL ethyl acetate. The aqueous solution was stripped to dryness under high vacuum. The solid residue was slurried with methanol and filtered. The crystals were washed with cold methanol, ether, and dried to give sodium (3S,4S)-3-benzyloxycarboxyamido-4-carbamoyloxymethyl-2-azetidinone-1-sulfonate in a yield of 36% by weight. The filtrate was concentrated and dissolved in 5 mL water, and then applied to a column of 60 mL Dianion, eluted with water and a mixture of 5% by volume ethanol and 95% by volume water. The desired fractions were combined, concentrated, and slurried with acetone to give additional 220 mg of sodium (3S,4S)-3-benzyloxycarboxamido-4-carbamoyloxymethyl-2-azetidinone-1-sulfonate.

EXAMPLE 11

Sodium (3S,4S) cis-3-[2-(2-Chloroacetamidothiazol-4-yl)-(Z)-2-(4-nitrobenzyloxycarbonylmethoxyimino)acetamido]-4-carbamoyloxymethyl-2-azetidinone-1-sulfonate To a solution of sodium (3S,4S) cis-3-benzyloxycarboxamido-4-carbamoyloxymethyl-2-azetidinone-1-sulfonate (15.7 g, 38 mmol) in water (237 ml) and THF (237 ml) was added 10% by weight palladium on 90% by weight carbon (15.7 g), and the mixture was stirred for 50 min in an atmosphere of hydrogen at room temperature. The catalyst was removed by filtration and washed with a mixture of water and THF (1:1 parts by volume, 474 ml). The filtrate and washings were combined and cooled to 0°–5° C. Tetrahydrofuran (237 ml), $NaHCO_3$ (7.66 g) and 2-(2-chloro acetamidothiazol-4-yl)-(Z)-2-(4-nitrobenzyloxycarbonylmethoxyimino)acetylchloride (23.33 g, 45.6 mmol) were added to the solution and the mixture was stirred for 50 min at 0°–5° C. After adjustment of pH to 5–6 was stirred for 160 min at room temperature. During the course of this reaction sodium N-methyldithiocarbamate was further added three times as follows; 5.89 g each after 40 min and 80 min and 1.5 g after 120 min. The pH of the reaction solution was kept under 7.5 by occasional additional of dil. aqueous HCl. After completion of the reaction the pH was adjusted to 5 and tetrahydrofuran was evaporated under a reduced pressure. The residual aqueous solution was washed with ether (300 ml) and concentrated under a reduced pressure. The residue was chromatographed on Diaion and eluted with water (10 liters), 10% EtOH (7 liters and 20% EtOH (12 liters). The fractions (ca. 10 liters) which contained the product were concentrated under a reduced pressure and the residue (ca. 750 ml) was lyophilized to give sodium (3S,4S) cis-3-[2-(2-chloroacetamidothiazol-4-yl)-(Z)-2-(4-nitrobenzyloxycarbonylmethoxyimino)acetamido]-4-carbamoyloxymethyl-2-azetidinone-1-sulfonate. (21.58 g, 82.4% yield).

EXAMPLE 12

(3S,4S) cis-3-[2-(2-Ammoniothiazol-4-yl)-(Z)-2-(carboxymethoxyimino)acetamido]-4-carbamoyloxymethyl-2-azetidinone-1-sulfonate To a solution of sodium (3S,4S) cis-3-[2-(2-chloroacetamidothiazol-4-yl)-(Z)-2-(4-nitrobenzyloxycarbonylmethoxyimino)acetamido]-4-carbamoyloxymethyl-2-acetidinone-1-sulfonate (21.4 g, 32.4 mmol) in water (1220 ml) was added 10% by weight Pd on 90% by weight carbon (50% wet, 21.4 g) and the mixture was stirred for 1 hour in an atmosphere of hydrogen at room temperature. The catalyst was removed by filtration and washed with a mixture of water and tetrahydrofuran (1:1 parts by volume, 1800 ml). The filtrate and washings were combined and concentrated under a reducd pressure. To the residue (ca. 600 ml) was added 3N HCl (35.6 ml), and the solution was stirred for 5 minutes, charged on the column of Diaion (5 liters) and eluted with water (7.5 liters) and 5% EtOH (13 liters). The fractions (ca. 5.5 liters) which contained (3S,4S)cis-3-[2-(-ammoniothiazol-4-yl)-(Z)-2-(carboxymethoxyimino)acetamido]-4-carbamoyloxymethyl-2-azetidinone-1-sulfonate were concentrated under a reduced pressure and the residue (ca. 750 ml) was lyophilized to give (3S,4S) cis-3-[2-(2-ammoniothiazol-4-yl)-(Z)-2-(carboxymethoxyimino)acetamido]-4-carbamoyloxymethyl-2-azetidinone-1-sulfonate (11.0 g, 70.0%) as a colorless powder.

The power (11 g) was suspended in cold water (220 ml), and the suspension was stirred for 2 hours at 0°–5° C. and then allowed to stand for 1 hour at the same temperature. The resulting colorless crystals were collected by filtration, washed with cold water (55 ml×2) and dried over $P_2O_5$ under a reduced pressure to give hemihydrate of (3S,4S) cis-3-[2-(2-ammoniothiazol-4-yl)-(Z)-2-(carboxymethoxyimino)acetamido]-4-carbamoyloxymethyl-2-azetidinone-1-sulfonate (9.8 g, 90% recovery).

EXAMPLE 13

2-O-(4-Chlorobenzenesulfonyl)-3,4-O-isopropylidene-L-threonamide

A solution of 3,4-O-isopropylidene-L-threonamide, 10.5 g (0.06M) and 24 mL triethylamine in 100 mL 1,2-dichloroethane at room temperature was added 19 g (0.09M) p-chlorobenzenesulfonyl chloride and the reaction mixture was stirred at room temperature for 30 hr. After the reaction, EtOAc (150 mL) was added and washed with 1N HCl, brine and 5% by weight aqueous $NaHCO_3$. The organic layer was separated and dried over $Na_2SO_4$ and recrystallized from EtOAc-Hexane to give 15.8 g (74%) of 2-O-(4-chlorobenzenesulfonyl)-3,4-O-isopropylidene-L-threonamide, mp 136°–138° C.

EXAMPLE 14

2-Azido-2-deoxy-3,4-O-isopropylidene-L-erythronamide

The mixture of 10.5 g (0.03M of 2-O-(4-chlorobenzenesulfonyl)-3,4-O-isopropylidene-L-threonamide and 2 g (0.036M) $NaN_3$ in DMF (30 mL) was heated at 60°–63° C. for 48 hr. After the reaction, the mixture was added to ethyl acetate (150 mL), filtered and the filtrate was washed with 5% aqueous $NaHCO_3$ and brine. The organic layer, dried over $Na_2SO_4$, was stripped to dryness and purified on high performance liquid chromatography ($CH_2Cl_2$-$CH_3CN$, 8:2) to give 2-azido-2-deoxy-3,4-O-isopropylidene-L-erythronamide (4.2 g, 70%), mp 98°–99° C.

EXAMPLE 15

(2S,3S)-2-Benzyloxycarboxamido-3-methanesulfonyloxy-4-(N-chloroacetylcarbamoyloxy)-butanamide A solution of 0.268 g (1 mM) of Nα-benzyloxycarbonyl-4-hydroxy-L-allothreoninamide in 5 mL DMF was cooled to −10° C. and 0.12 g (1 mM) chloroacetylisocyanate was added and the reaction was stirred at −10° C. for 1 hr to give (2S,3S)-2-benzyloxycarboxamido-3-hydroxy-4-(N-chloroacetylcarbamoyloxy-butanamide. To the above reaction mixture, 0.148 g (1.25 mM) methanesulfonylchloride was added at −15° to −10° C. and 0.26 mL triethylamine was added subsequently. The reaction mixture was stirred at −15° to −10° C. for 40 min. After the reaction, ethylacetate (20 mL) was added. The resulting mixture was washed with 5% aqueous $NaH_2PO_4$, brine and the organic layer was dried over $Na_2SO_4$. Solvent was removed at the reduced pressure and the crude product was purified by column chromatograph ($SiO_2$, EtOAc:-Hexane-8:2) to give (2S,3S)-2-benzyloxycarboxamido-3-methanesulfonyloxy-4-(N-chloroacetylcarbamoyloxy)-butanamide 0.25 g (53%).

EXAMPLE 16

Sodium (3S,4S)-3-benzyloxycarboxamido-4-carbamoyloxymethyl-2-azetidinone-1-sulfonate To the solution of 0.3 ml (3.0 mM) 2-picoline and 0.1 mL (1.5 mM) chlorosulfonic acid in dichloromethane (8 mL) was added 0.24 g (0.51 mM) (2S,3S)-benzyloxycarboxamido-3-methanesulfonyloxy-4-(N-chloroacetylcarbamoyloxy)-butanamide and the solution was heated at 45° C. for 18 hr to produce the picolinium (3S,4S)-2-benzyloxycarboxamide-3-methanesulfonyloxy-4-(N-chloroacetylcarbamoyloxy)-butanamide N-sulfonate. After the reaction, water (15 mL) was added to the reaction mixture and pH was adjusted to 7–8. The aqueous layer was stirred with 0.074 g (0.5 mM) sodium N-methyldithiocarbamate at room temperature for 4 hr. The pH was then adjusted to 3 with $NaHSO_3$ and washed with ethyl acetate. To the aqueous layer, 0.30 g (0.75 mM) tetrabutylammonium bisulfate was added and the mixture was extracted with methylene chloride (20 mL×2). The organic layer dried over $Na_2SO_4$, was evaporated at reduced pressure to give tetrabutylammonium (2S,3S)-2-benzyloxycarboxamido-3-methanesulfonyloxy-4-carbamoyloxy-butanamide N-sulfonate which was used for the next step without further purification.

To the solution of this sulfonate in 10 mL $CH_2Cl_2$ was added 168 mg $NaHCO_3$ in water (4 mL) and the mixture was heated at 85° C. with vigorous stirring for 15 min. The methylenechloride layer was concentrated and the residue was dissolved in 3 mL of ethanol. The ethanol solution was then treated with AG 50W X4 ($Na^+$ form), to give the sodium salt of sodium (3S,4S)-3-benzyloxycarboxamido-4-carbamoyloxymethyl-2-azetidinone-1-sulfonate (30 mg, 7.5%), and by-product sodium (3S,4S) cis-3-benzyloxycarboxamido-4-hydroxymethyl-2-azetidinone-1-sulfonate (20 mg). This mixture was crystallized from methanol-water (2 ml:0.5 ml) to give the pure sodium (3L S,4S), cis-3-benzyloxycarboxamido-4-carbamoyloxymethyl-2-azetidinone-1-sulfonate. The mother liquor was added 28 mg (0.07 mM) of tetrabutylammonium bisulfate and extracted with $CH_2Cl_2$ to give tetrabutylammonium (3S,4S) cis-3-benzyloxycarboxamido-4-hydroxymethyl-2-azetidinone-1-sulfonate.

EXAMPLE 17

Sodium (3S,4S) cis-3-benzyloxycarboxamido-4-carbamoyloxymethyl-2-azetidinone-1-sulfonate A solution of 0.57 g (1 mM) (3S,4S)-3-benzyloxycarboxamido-4-hydroxy-methyl-2-azetidinone-1-sulfonate (tetrabutylammonium salt) in 10 mL $CH_2Cl_2$ (dry) was added 0.24 g (2 mM) chloroacetylisocyanate at 0° C. and then stirred at 0° C. for 45 min. After the reaction, solvent was removed at reduced pressure and the residue was dissolved in 10 mL THF, 2 mL 5% aqueous $NaHCO_3$ and 0.2 mL methanol. The mixture was heated with stirring at 45° C. for 5 hr. After the reaction, the residue was dissolved in chloroform (20 mL). The chloroform solution, washed with brine, was stripped to dryness and the residue was dissolved in 10 mL EtOH-$H_2O$ (1:2 parts by volume) and then treated with AG 50W-X4 (4 mL, $Na^+$ form). The resin was filtered off and the filtrate was concentrated under high vacuum. Crystallization from acetone-$H_2O$ gave 113 mg (29%) of sodium (3S,4S)-3-benzyloxycarboxamido-4-carbamoyloxymethyl-2-azetidinone-1-sulfonate. The mother liquor was purified on Diaion to give another 30 mg (8% yield) of product.

EXAMPLE 18

Calcium-L-threonate

Into a 12-L flask equipped with stirrer, thermometer, additional funnel was charged 528 g L-ascorbic acid (3.0 moles) and 7500 mL distilled water. The batch was stirred at room temperature to form a clear solution and added 600 g calcium carbonate. The slurry was stirred and cooled to 15° C. Then 1200 mL hydrogen peroxide (30% w/w) was added at 12°–15° C. over 60 min. The mixture was stirred at room temperature for 16 h. Then 120 g charcoal was added. The mixture was heated to 75° C. while stirring was continued until no more oxygen was evolved (as indicated by bubbling in a water trap). The batch was filtered at 70°–75° C., and the filter cake washed with 2×100 mL distilled water. The combined filtrate was concentrated to about 2-L at less than 50° C. under vacuum. Then 1500 mL methanol was added until the solution became cloudy. The mixture was then stirred at room temperature for 16 h, filtered, and washed with 2×100 mL methanol. The solids were dried at 60° C. under vacuum to constant weight to obtain calcium-L-threonate monohydrate having a dry weight of 436.5 g and a melting point 300+° C.

Recrystallization:

Into a 12-L flask equipped with stirrer, thermometer, reflux condenser were charged 400 g crude calcium-L-threonate and 6000 mL distilled water. The batch was stirred and heated to 92° C. until a cloudy solution was obtained. The batch was filtered at 90° C., and the filter residue was washed with 100 mL distilled water. The combined filtrate was concentrated to about 2-L, then about 2000 mL methanol was added until the batch was cloudy. It was then stirred at room temperature for 16 h, filtered, washed with 2×100 mL methanol. The solids were dried until constant weight at 60° C. under vacuum to produce 376.9 grams of recrystallized calcium-l-threonate monohydrate.

EXAMPLE 19

L-Threonolactone

Into a 2-L round bottom flask were placed 46.73 g calcium threonate monohydrate and 1000 mL water. The mixture was heated on a steam bath until complete dissolution was achieved (30 min). Then 300 mL Bio-Rad resin AG 50W-X4 (H+-form) was added. The hot mixture was vigorously stirred for 30 min, the solids were filtered off and the filtrate was evaporated to dryness under high vacuum. The residue was resuspended and azeotropically evaporated (on the rotary evaporator) twice with acetonitrile. The residue was then suspended in 500 mL acetonitrile, and 1 g p-toluenesulfonic acid was added. The mixture was heated at reflux temperature for 1 h. It was then cooled and filtered. The filtrate was evaporated and the residue was crystallized from acetonitrile/ether. As a result 25.07 g white crystals of L-threonolactone were collected after refrigeration overnight. The mother liquor was evaporated and the residue was dissolved in about 100 mL ethyl acetate and washed with 2% by weight aqueous sodium bicarbonate, dried over $Na_2SO_4$ and evaporated. The residue was recrystallized from $CH_3CN/Et_2O$ to afford an additional L-threonolactone 568 mg white crystals; mp 66° C.; total yield 76%.

EXAMPLE 20

L-Threonamide

A solution of 5.50 g (46.57 mmoles) L-threonolactone in 100 mL MeOH, previously saturated with anhydrous $NH_3$ at 0° C., was kept at room temperature for 48 h in a pressure bottle. The solvent was evaporated in vacuo, the residual oil re-evaporated from absolute EtOH, and the resulting solid crystallized from boiling EtOH. The crystals were collected after cooling at 0° C., washed with EtOH-$Et_2O$ (1:1 parts by volume), then with $Et_2O$, and dried at 40° C./0.005 mm Hg to give 6.023 g (95.7%) of analytically pure product L-threonamide, m.p. 105°–107° C.

EXAMPLE 21

3,4-O-Isopropylidene-L-threonamide

To a solution of 5.00 g (37 mmoles) L-threonamide dissolved in 50 mL dry DMF (4A molecular Sieves) was added 16.38 mL (132.2 mmoles) of 2,2-dimethoxypropane and 120 mg (0.63 mmoles) of p-toluenesulfonic acid monohydrate, and the solution was stirred at room temperature under argon for 4.5 h. The reaction was then stirred with 2.5 g of Dowex AG 1-X4 (OH-form, 100–200 mesh), for 2 min, the residue removed by filtration, and the combined filtrate and washings (DMF) were evaporated in vacuo (oil pump) finally at 55° C. to give a colorless syrup. Crystallization from ethylacetate-ether-hexane afforded 3.600 g (55.5%) of pure 3,4-O-isopropylidene-L-threonamide as colorless crystals. Flash chromatography of the residue from the mother liquors on silica gel 60, using a 50×5.4 cm column (filled to 27 cm), gave first 0.560 g of a diisopropylidene derivative, eluted with ethylacetate-acetonitrile (100:15 parts of volume), and then an additional 0.613 of the desired product (after crystallization), eluted with ethylacetate-acetonitrile (100:30 parts by volume). The total yield was 4.21 g of 3,4-O-isopropylidene-L-threonamide (65%).

We claim:

1. A compound of the formula

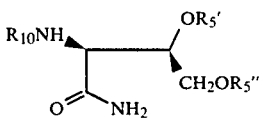

wherein $R_5'$ and $R_5''$ are hydrogen, or taken together with their attached oxygen atoms form an acetal or ketal protecting group having the formula

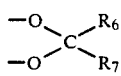

wherein $R_6$ and $R_7$ are hydrogen, lower alkyl, lower alkoxy or taken together form oxo or lower alkylene; $R_{10}$ is hydrogen or an amino protecting group selected from lower alkoxy carbonyl, aryloxy carbonyl, halo substituted lower alkoxy carbonyl, or arylloweralkoxy carbonyl, with the proviso that when $R_{10}$ is hydrogen, $R_5'$ and $R_5''$ are other than hydrogen.

2. The compound of claim 1 wherein $R_5'$ and $R_5''$ are hydrogen.

3. The compound of claim 1 wherein $R_{10}$ is benzyloxycarbonyl, nitro substituted benzyloxycarbonyl, lower alkyl substituted benzloxycarbonyl, halo substituted benzyloxycarbonyl.

4. The compound of claim 3 wherein said compound is Nα-benzyloxycarbonyl-4-hydroxy-L-allo-threoninamide.

5. The compound of claim 1 wherein said compound is 2-N-benzyloxycarbonyl-amino-2-deoxy-3,4-O-isopropylidene-L-erythronamide.

6. The compound of claim 1 wherein said compound is 2-amino-2-deoxy-3,4-O-isopropylidene-L-erythronamide.

* * * * *

UNITED STATES PATENT AND TRADEMARK OFFICE
CERTIFICATE OF CORRECTION

PATENT NO. : 4,663,469
DATED : May 5, 1987
INVENTOR(S) : Chung-Chen Wei and Manfred Weigele It is certified that error appears in the above-identified patent and that said Letters Patent is hereby corrected as shown below:

Column 4, lines 50-54, Formula IX should appear as follows:

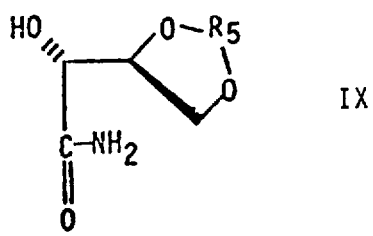

UNITED STATES PATENT AND TRADEMARK OFFICE
CERTIFICATE OF CORRECTION

PATENT NO. : 4,663,469
DATED : May 5, 1987
INVENTOR(S) : Chung-Chen Wei and Manfred Weigele It is certified that error appears in the above-identified patent and that said Letters Patent is hereby corrected as shown below:

Column 4, lines 61-69, Formula XI should appear as follows:

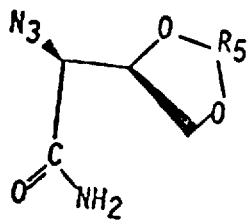

XI

Signed and Sealed this

Twenty-eighth Day of April, 1992

*Attest:*

HARRY F. MANBECK, JR.

*Attesting Officer*  *Commissioner of Patents and Trademarks*